United States Patent [19]

Witsoe

[11] 4,331,540
[45] May 25, 1982

[54] PROCESS FOR DRAINING DIALYSATE FROM ARTIFICIAL KIDNEY

[75] Inventor: David A. Witsoe, Libertyville, Ill.

[73] Assignee: Baxter Travenol Laboratories, Inc., Deerfield, Ill.

[21] Appl. No.: 142,602

[22] Filed: Apr. 21, 1980

[51] Int. Cl.³ .................... B01D 13/00; B01D 31/00
[52] U.S. Cl. ............................. 210/646; 210/321.3; 210/248; 137/1; 137/565
[58] Field of Search ............. 210/600, 646, 647, 248, 210/321.1, 321.2, 321.3, 321.4, 321.5; 137/1, 565

[56] References Cited

U.S. PATENT DOCUMENTS

| | | | |
|---|---|---|---|
| 2,969,150 | 1/1961 | Broman | 210/321.5 |
| 2,987,188 | 6/1961 | Jahreis | 210/248 |
| 4,060,485 | 11/1977 | Eaton | 210/321.2 X |
| 4,153,554 | 5/1979 | von der Heide et al. | 210/135 X |
| 4,180,460 | 12/1979 | Calari | 210/182 |
| 4,190,047 | 2/1980 | Jacobsen et al. | 210/646 X |
| 4,229,299 | 10/1980 | Savitz et al. | 210/137 X |

OTHER PUBLICATIONS

"Artificial Kidneys", Art. Organs Division, Travenol Labs. Morton Grove, Ill., Jul. 5, 1967.

Primary Examiner—Charles N. Hart
Assistant Examiner—David R. Sadowski
Attorney, Agent, or Firm—Paul C. Flattery; Thomas R. Schuman; Gerald S. Geren

[57] ABSTRACT

There is disclosed herein a dialysis machine: (a) to which a negative pressure dialyzer can be connected; and (b) which can be operated so as to drain the dialysis solution from the dialyzer through the lower of the dialysis solution inlet and outlet ports. This apparatus and method permit a dialyzer to be drained of dialysis solution at the end of the dialysis treatment session in such a manner as to prevent spillage and leakage associated with the removal of the dialyzer from the machine.

3 Claims, 4 Drawing Figures

PROCESS FOR DRAINING DIALYSATE FROM ARTIFICIAL KIDNEY

FIELD OF THE INVENTION

This invention relates to artificial kidney systems, and more particularly, to an apparatus and method for draining dialysis solution from a dialyzer after dialysis.

BACKGROUND OF THE INVENTION

Artificial kidney systems usually include a dialyzer and a dialysis machine which controls the operation of the dialyzer. The dialyzer is used to treat a patient's blood so as to remove water and waste products therefrom. Such dialyzers include a semipermeable membrane which separates the blood and the dialysis solution flowing through the dialyzer. Waste product removal occurs by mass transfer through the membrane, and water removal occurs by ultrafiltration through the membrane.

Some dialysis machines operate to draw the dialysis solution through the dialyzer under a negative pressure (i.e., below atmospheric pressure). These machines normally include: (a) a negative-pressure-type pump positioned downstream of the dialyzer for drawing the dialysis solution from a source through the dialyzer; and (b) adjustable restrictions positioned upstream and downstream of the dialyzer for controlling the flow rate and the negative pressure on the dialysis solution within the dialyzer.

U.S. Pat. No. 3,878,095 Frasier et al discloses a negative-pressure-type dialysis machine of that type. A commercial machine embodying such a system is manufactured and sold by Baxter Travenol Laboratories and is identified as Proportioning Dialyzing Fluid Delivery System (5M 1352–5M 1355).

Two types of negative pressure dialyzers which are commercially available are known as hollow-fiber dialyzers and as capillary-film dialyzers. Each of these dialyzers has two spaced dialysis solution ports and two spaced blood ports. These dialyzers are sold by Baxter Travenol Laboratories as the CF ® hollow-fiber dialyzer and the HD TM capillary-film dialyzer.

Presently, during dialysis the dialyzer is supported on a bracket and flexible conduits connect the machine to the dialysis solution inlet and outlet. When the dialysis session is completed, dialysis solution remains in the dialyzer and must be drained. Presently, one technique is to clamp the conduits leading to and from the dialyzer, remove the dialyzer and then drain or discard it. Another technique is to rotate the dialyzer to a horizontal position to minimize leakage and then the operator using her fingers can close the ports and carry the dialyzer to a sink where the dialysis solution can be drained. While somewhat inconvenient, these techniques have been acceptable.

New dialysis machines are becoming commercially available in which the dialyzer is securely and directly connected to the machine without the flexible conduits and with the dialysis solution ports positioned one above the other. At the end of a dialysis session when the dialyzer is disconnected, there is substantial dialysis solution leakage or spillage since there are no hoses to be clamped, and during the removal and horizontal positioning, there is substantial spillage. This result in unacceptable in that the spillage must be cleaned, which is time-consuming, and otherwise generally undesirable.

It is therefore the object of this invention to provide an apparatus and technique for use with the new dialysis machines to permit drainage of the dialyzer after dialysis while preventing spillage.

These and other objects will become apparent from the following description and appended claims.

SUMMARY OF THE INVENTION

There is disclosed herein a dialysis machine: (a) to which a negative pressure dialyzer can be connected; and (b) which can be operated so as to drain the dialyzer through the lower of the dialysis solution inlet and outlet ports and the machine itself, and thereby avoid dialysis solution spillage.

The machine has a flow system which includes: a source of fresh dialysis solution; and a negative pressure pump for drawing the dialysis solution through a series of valves, through the dialyzer and then for discharging the spent dialysis solution to drain. The dialyzer's dialysis solution inlet and outlet ports are directly and securely connected to the machine, and in order to drain the dialyzer, the valves are operated so as (1) to prevent any dialysis solution flow to the dialyzer and (2) to apply a negative pressure to the lower of the dialysis solution inlet and outlet ports. The upper of the inlet and outlet ports is vented, preferably to atmosphere, so that said negative pressure will draw and drain the dialysis solution from the dialyzer. The dialysis solution is then routed through the machine to the drain to which the machine is connected. This eliminates dialysis solution spillage, clean-up and related problems associated with dialyzer removal.

It is anticipated that adapters will be provided for the new dialysis machines so that existing dialyzers may be coupled to the machine through a hose extender system. The drainage system disclosed herein can also be utilized with such hose extender system.

DESCRIPTION OF THE PREFERRED EMBODIMENT

The Flow System

Figure 1:
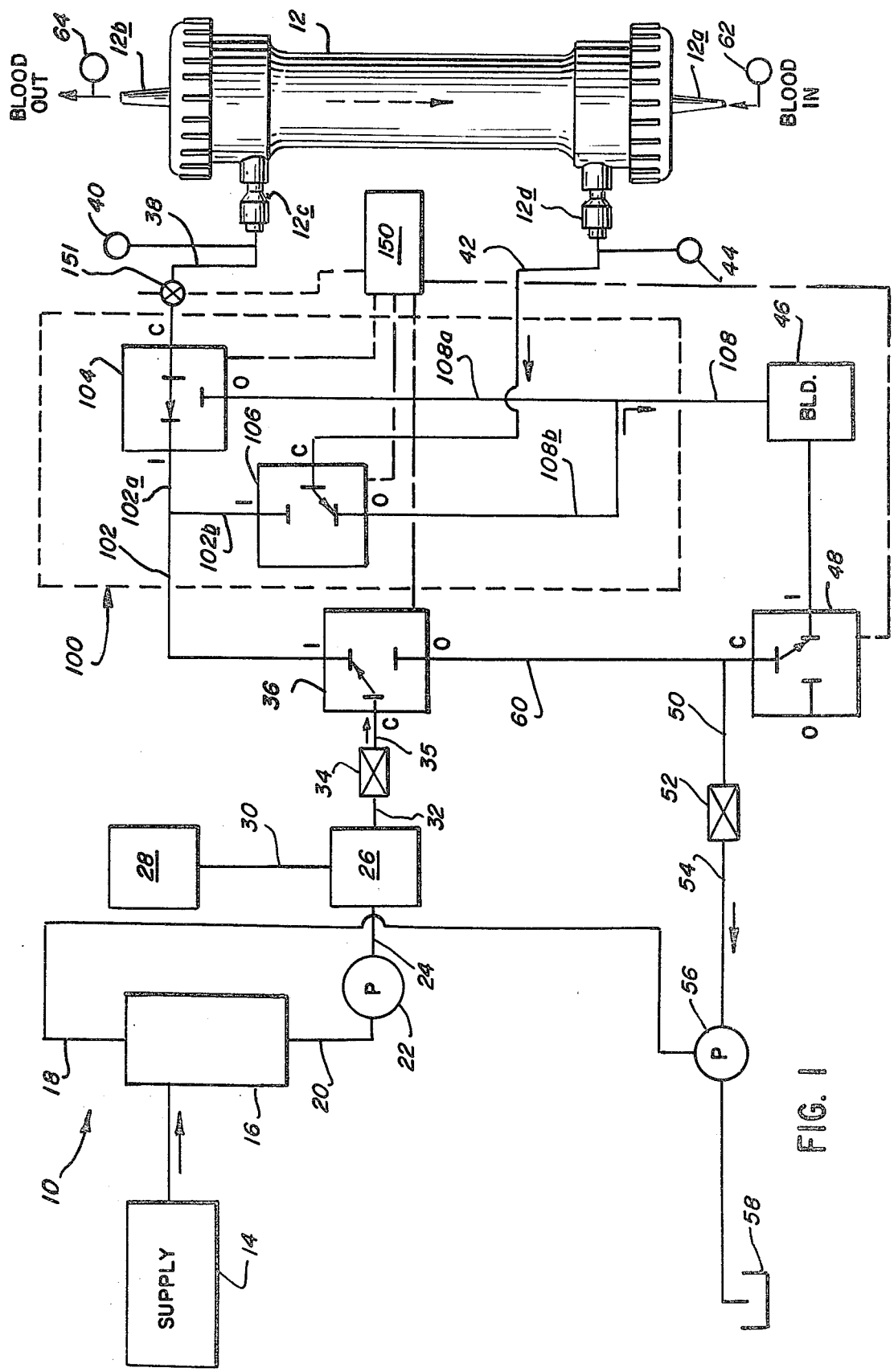
FIG. 1 is a diagrammatic view of the flow system of the machine with which the drainage system is employed with the valving shown in a normal flow mode.

Referring now to FIG. 1, the dialysis flow system 10 generally is shown connected to a CF ® or hollow-fiber dialyzer 12 generally. The dialyzer is elongated and has a pair of spaced blood ports 12a and 12b and a pair of spaced dialysis solution ports 12c and 12d.

The dialyzer is vertically oriented, such that during dialysis, blood enters through the inlet 12a and flows upwardly to the blood outlet 12b, while dialysis solution enters through the port 12c and flows downwardly through the port 12d.

The flow system includes a water supply 14 from which the water flows to a degassing tank 16. Air is withdrawn from the top of the tank 16, through line 18 and degassed liquid is drawn from the bottom of the tank via line 20 by the pump 22. Details of this degassing system are shown in British Pat. GB No. 1,501,956, the disclosure of which is incorporated herein by reference. Briefly, that system is capable of applying negative pressures as low as −700 mm Hg to the liquid in the tank, the result of which is a very effectively degassed liquid.

The degassed liquid flows from pump 22 via line 24 to a mixing site 26 where the degassed liquid mixes with dialysis solution concentrate entering the site 26 from the concentrate supply 28 via line 30. The dialysis solution then flows from the site 26 via line 32 to a flow restriction 34. This restriction cooperates in controlling flow to the dialyzer 12. From the restriction 34, liquid flows via line 35 to a three-way flow control valve 36 which is sometimes referred to as the "to" valve ("to" referring to the fact that the dialysis solution flows "to" the dialyzer through the valve 36). Valve 36 has three ports, identified as "C", "1" and "0" and line 35 connects to the "C" port. When deactivated, the "C" and the "0" ports are connected, and when activated, the "C" and the "1" ports are connected.

Dialysis solution exits the valve 36 from port "1" and flows through a flow reversing valving mechanism 100 (which is shown in the dashed lines), and during dialysis via line 38 to the dialysis solution port 12c. A dialysis solution pressure transducer 40 is provided for detecting the dialysis solution pressure in the line 38.

The flow reversing mechanism 100 permits selection of dialysis solution flow direction through the dialyzer, usually in a downward direction or an upward direction, depending upon whether a hollow-fiber or capillary-film dialyzer is in use and whether the machine is in a set-up or normal operation mode.

During dialysis, dialysis solution flows downwardly through the dialyzer and exits via port 12d. Spent or used dialysis solution then flows from the port 12d via line 42 back through the flow reversing mechanism 100. A second pressure transducer 44 is provided for detecting the dialysis solution pressure in line 42.

The dialysis solution exits the flow reversing mechanism 100 and flows through a blood leak detector 46 and then through a second valve 48, which is sometimes referred to as the "from" valve. This valve also has "C", "1" and "0" ports and related activated and deactivated positions. In this valve, port "0" is plugged so as to prevent flow therethrough and the valve thus acts as an on/off switch. The blood leak detector 46 is positioned downstream of the flow reversing mechanism so as to detect any blood which passes through the semipermeable membrane into the dialysis solution. Detection of such blood activates various alarm conditions and prevents further dialysis until the condition is corrected.

Spent dialysis solution enters from the valve 48 at port "1", exits at port "C" and then flows via line 50 to a second flow or pressure-relating restriction 52. The solution then flows via line 54 to the negative-pressure or effluent pump 56 which then discharges the spent dialysis solution to drain 58.

The pump 56 is also connected to line 18 and creates the negative pressure for withdrawing gas from the upper portion of the degassing tank 16.

A bypass line 60 is provided and is connected to each of the valves 36 and 48 so as to permit dialysis solution flow to bypass the dialyzer. In the event it is necessary or desirable to cause dialysis solution to bypass the dialyzer, the ports "C" and "0" of valve 36 are connected and ports "C" and "1" of valve 48 are disconnected. This prevents dialysis solution from flowing to the dialyzer 12 and directs dialysis solution through the bypass line 60 and directly to drain.

On the blood side of the dialyzer, the arterial blood pressure is detected by the arterial blood pressure transducer 62 and the venous blood pressure is detected by the venous blood pressure transducer 64.

Flow Reversing System

Referring now to the flow reversing mechanism 100 as shown in FIG. 1, dialysis solution enters the mechanism from the valve 36 via line 102. Line 102 divides into a first branch 102a and a second branch 102b. Branch 102a connects to the "1" port of a first three-way valve 104 and the branch 102b connects to the "1" port of a second three-way valve 106.

The "0" port of valve 104 is connected to the branch 108a of the outlet line 108 and the "0" port of valve 106 is connected to branch 108b of the outlet line 108. The "C" port of valve 104 is connected to line 38 and dialyzer port 12c, while the "C" port of valve 106 is connected to line 42 and dialyzer port 12d.

Each of the valves 104 and 106 are of identical construction and are arranged such that in the deactivated position the "C" port is connected to the "0" port, and in the activated position, the "C" port is connected to the "1" port. It should be noted that each of the "1" ports are connected to the inlet line branch, the "0" ports are connected to the outlet line branch, and the "C" ports are connected to the dialyzer.

The following table summarizes the positioning of the flow reversing valves 104 and 106, during set-up and normal use, with a hollow-fiber dialyzer, with a capillary-film dialyzer and when the machine is not operating:

| Dialyzer Type | Flow Condition | Valve 104 | Valve 106 |
| --- | --- | --- | --- |
| Hollow fiber | Normal | Activated (C - 1) | Deactivated (C - 0) |
| Hollow fiber | Set-up | Deactivated (C - 0) | Activated (C - 1) |
| Capillary film | Normal | Deactivated (C - 0) | Activated (C - 1) |
| Capillary film | Set-up | Activated (C - 1) | Deactivated (C - 0) |
|  | Machine Not Operating | Deactivated (C - 0) | Deactivated (C - 0) |

Set-up refers to the period before actual dialysis during which air is removed from the dialyzer prior to dialysis, the blood side of the dialyzer is primed, and the dialyzer is otherwise "conditioned" for actual dialysis. Normal refers to the direction of dialysis solution flow through the dialyzer during actual dialysis. Sometimes during dialysis it may be desirable to briefly reverse the direction of dialysis solution flow to remove any built-up gas, and this can be done by reversing the direction of flow.

Dialyzer Drainage

Figure 2:
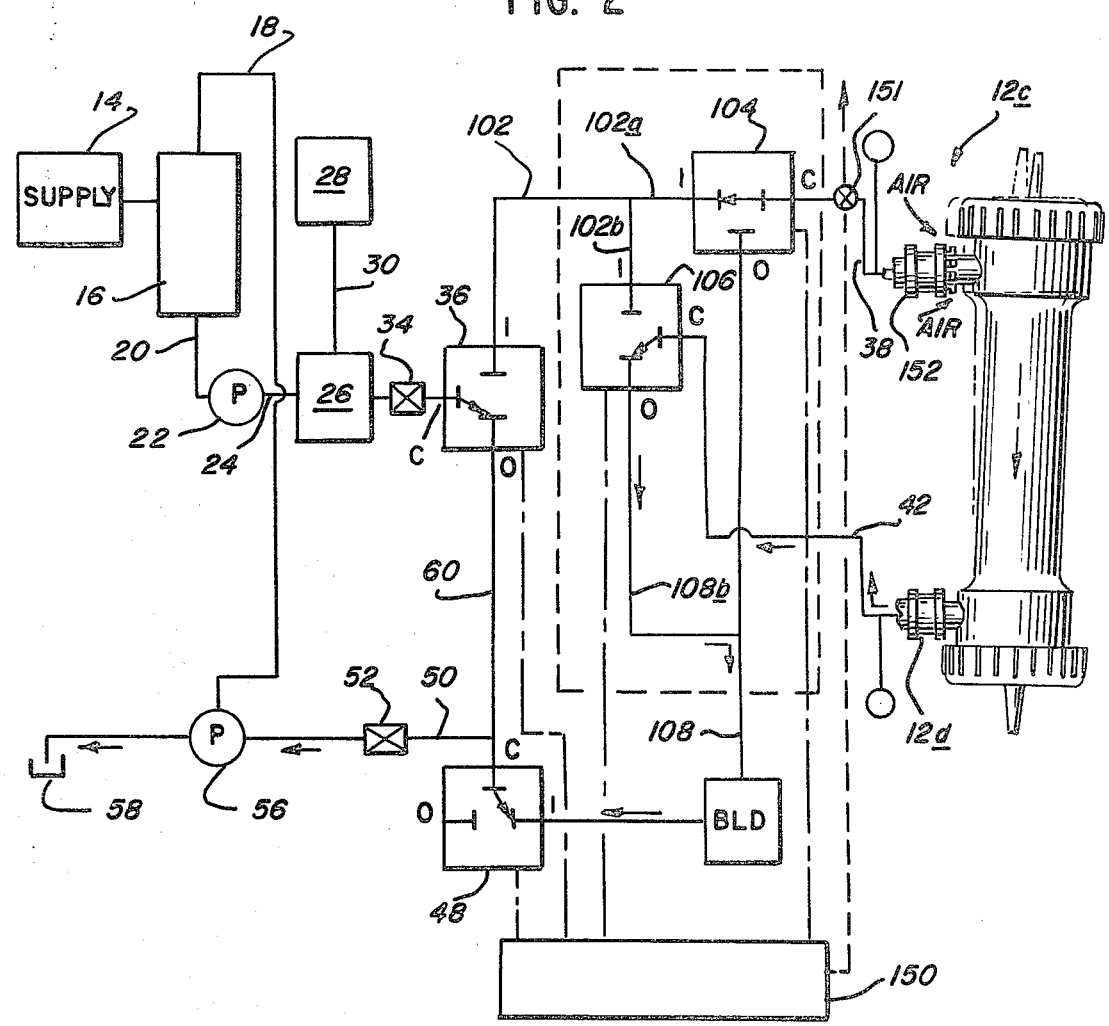
FIG. 2 is a diagrammatic view showing the valving in the drain mode and the dialyzer tipped to permit venting.

Referring now to FIG. 2, at the end of a dialysis session, the valves are operated so as to (a) deactivate the "to" valve 36 by connecting ports "C" and "0"; (b) activate the "from" valve 48 by connecting ports "C" and "1"; (c) activate valve 104 by connecting ports "C" and "1"; and (d) deactivate valve 106 by connecting ports "C" and "0". With the valves so connected, dialysis solution cannot flow to the dialyzer since the pump 56 draws the dialysis solution through the "to" valve 36, through bypass line 60, and then through line 50, restriction 52 and line 54. Since the "to" valve 36 is deactivated, communication between the pump 56 and the upper dialysis solution port 12c is interrupted. Thus negative pressure is not applied to port 12c through valve 36, line 102, branches 102a or 102b, valve 104 and line 38.

However, the pump 56 in addition to drawing dialysis solution through lines 60 and 50 also creates a negative pressure at valve 48. Since valve 48 is in the activated position, that negative pressure acts on the lower dialysis solution port 12d, through the valve 48, the blood leak detector 46, the line 108, branch 108b, through valve 106 via ports "0" and "C" and line 42.

Thus, with the valves in the foregoing arrangement: dialysis solution cannot flow to the dialyzer; communication between the pump 56 and upper dialyzer port 12c is interrupted so that the pump does not directly apply a negative pressure to the upper port 12c; and the pump 56 and lower dialyzer port 12d are connected so that the pump applies a negative pressure directly to the lower port.

However, in order to drain the dialyzer, it is necessary to vent the upper dialyzer port 12c, preferably directly to atmosphere. This can be done by manually opening the connection between the upper port and the machine. "Hansen" connectors, such as 152, are used to connect the dialyzer and machine. Thus by simply opening the connector 152 so as to release its grasp on the dialyzer and then separating the dialyzer from the connector, the seal between the machine and dialyzer is broken and air can enter the dialyzer through the upper port 12c and the dialyzer is thereby "vented".

Alternatively, an automatic venting valve, such as 151, can be provided in the line 38 between valve 104 and upper port 12c which valve will vent the dialyzer to atmosphere, when in the drainage mode, without opening the connector 152.

Once the dialyzer is vented, the pump 56 can drain dialysis solution from the dialyzer by drawing dialysis solution therefrom for discharge to drain 58. The dialyzer will be drained until only a small amount of dialysis solution is left at the bottom of the dialyzer in the header portion below the lower port 12d. The dialysis machine is then placed in the bypass mode with both the "to" and "from" valves 36 and 48 in the deactivated condition (i.e., "C" and "0" ports connected). The connector for the lower port 12d is then released and the dialyzer 12 is then removed from the machine. The small amount of remaining dialysis solution can be manually drained without the spillage associated with prior techniques.

The foregoing valve sequencing can be accomplished manually by individual valve controls; or by automatic control means 150 which automatically operates the valves 36, 48, 102 and 104 in their various modes as well as the vent valves 151.

The Connector

Figure 3:
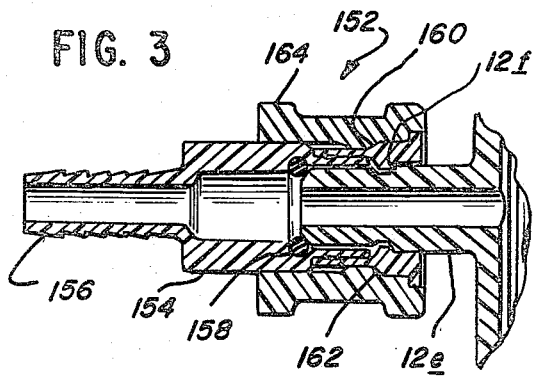
FIG. 3 is a cross-sectional view showing the connection between the dialyzer and machine and the connector in the locked position.
Figure 4:
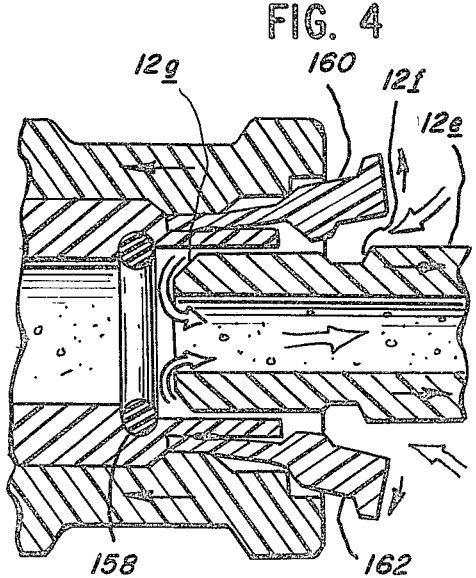
FIG. 4 is an enlarged cross-sectional view showing the connector in an open and venting position.

Referring now to FIGS. 3 and 4, connection of the dialyzer to the machine may be made by the use of a nipple, such as 12e, on the dialyzer 12 and the slide connector assembly 152, which is sometimes known as a Hansen connector and which is associated with the machine. The nipple 12e has a locking groove 12f between the nipple ends with the outer nipple end 12g beveled for forming a seal seat.

One type of suitable connector is manufactured by the Hansen Manufacturing Co. of Cleveland, Ohio, and is identified as a Series 3-ST. The connector includes: a tubular inner member 154 having a barbed small-diameter end 156 for connection to the machine or flexible tubing; an intermediate O-ring seal 158; and a plurality of flexible groove-grasping fingers, such as 160 and 162, at the other or large-diameter end. The other member 164 is a slidable locking collar which fits about the inner member for locking the fingers to the connector with the fingers grasping the groove. The collar 164 is slidable toward the large-diameter end for locking the fingers, such as 160 and 162, into the groove 12f so as to sealingly lock the connector to the nipple.

By sliding the collar 164 toward the barbed or machine end, the fingers are released and the seal may be broken. This operation permits manual venting of the dialyzer.

It will be appreciated that numerous changes and modifications can be made to the embodiment shown herein without departing from the spirit and scope of the invention.

What is claimed is:

1. A method of draining dialysis solution from a negative-pressure-type dialyzer which is connected to a dialysis machine;

where the dialyzer has a dialysis solution inlet and a dialysis solution outlet, each of which during dialysis is directly connected to the machine and one of which is positioned above the other; and where the dialysis machine includes a dialysis solution flow path whereby liquid is drawn under a negative pressure by pump means, from a supply through valve means, through said dialyzer and then flows to a drain, said method comprising the steps of:

operating said valve means so as to apply a negative pressure to the lower of said inlet and outlet, while preventing flow of dialysis solution to each of said inlet and outlet; and venting the upper of said inlet and outlet so as to permit said negative pressure to drain said dialysis solution therefrom;

wherein said valve means include:

(a) to-valve means having an activated position in which said supply is in fluid communication with said dialyzer and a deactivated position in which said supply is in communication with said pump means;

(b) from-valve means having an activated position in which said pump means and dialyzer are in fluid communication and a deactivated position in which said communication is interrupted;

(c) flow reversing valve means communicating with said dialyzer and said to-valve means and from-valve means for controlling the direction of dialysis solution flow in the dialyzer;

wherein said flow reversing valve means includes a first three-way valve and a second three-way valve, each of which communicates with said to-valve means and said from-valve means and with the first three-way valve communicating with the upper dialysis solution port and the second-three way valve communicating with the lower dialysis solution port; said method further comprising the steps of operating said valve means, such that said first three-way valve is positioned to communicate with the upper port and the to-valve means;

second three-way valve is positioned to communicate with the lower port and the from-valve means;

to-valve means is deactivated and communicates with the pump means; and from-valve means is activated and communicates with the pump means and the second three-way valve.

2. A method as in claim 1, wherein said valves are automatically operated.

3. A method as in claim 1, wherein said dialysis machine includes venting valve means arranged for cooperation with the upper of said inlet or outlet and for venting of said dialyzer.

* * * * *